United States Patent [19]

Cooper et al.

[11] Patent Number: 4,490,370

[45] Date of Patent: Dec. 25, 1984

[54] NAPHTHYLGLYCYL CEPHALOSPORIN DERIVATIVES

[75] Inventors: Robin D. G. Cooper; Larry C. Blaszczak, both of Indianapolis; Jan R. Turner, Carmel, all of Ind.

[73] Assignee: Eli Lilly and Company, Indianapolis, Ind.

[21] Appl. No.: 484,128

[22] Filed: Apr. 12, 1983

[51] Int. Cl.$^3$ .................. A61K 31/545; C07D 501/22
[52] U.S. Cl. ........................................ 424/246; 544/16; 544/21; 544/29; 544/30
[58] Field of Search .................... 424/246; 544/30, 16, 544/21, 29

[56] References Cited

U.S. PATENT DOCUMENTS

| | | | |
|---|---|---|---|
| 3,364,212 | 1/1968 | Patchett | 260/243 |
| 3,518,260 | 6/1970 | Spencer et al. | 260/243 |
| 3,560,489 | 2/1971 | Morin | 260/243 |
| 3,994,884 | 11/1976 | Weir | 260/243 C |
| 4,079,178 | 3/1978 | Cook et al. | 424/246 |

*Primary Examiner*—Paul M. Coughlan, Jr.
*Attorney, Agent, or Firm*—Charles W. Ashbrook; Arthur R. Whale

[57] ABSTRACT

Naphthylglycyl and tetrahydronaphthylglycyl cephalosporins are potent antibacterial agents and are particularly useful as oral treatments for upper respiratory infections.

40 Claims, No Drawings

NAPHTHYLGLYCYL CEPHALOSPORIN DERIVATIVES

BACKGROUND OF THE INVENTION

The cephalosporin class of antibiotics has been extensively studied, and several members of the class are now routinely used to combat bacterial diseases caused by a broad spectrum of gram positive and gram negative microorganisms. The majority of such compounds are not effective orally, but rather are administered intramuscularly or intravenously, thus necessitating assistance from medically trained personnel. Moreover, since the compounds are effective against a broad spectrum of microorganisms, they generally are not employed for their specificity.

There remains a need for cepahlosporin antibiotics that are orally effective and have a degree of specificity toward one or more groups of microorganisms. An object of this invention is to provide a group of compounds that satisfy these needs.

SUMMARY OF THE INVENTION

This invention concerns cephalosporin antibiotics. The invention is more particularly directed to a group of orally active 2-naphthylglycyl cephalosporins having the formula

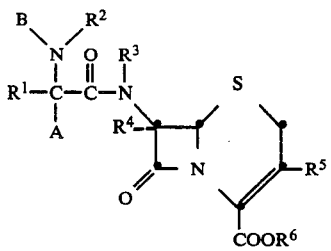

wherein:
$R^1$ is

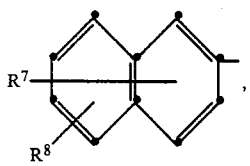

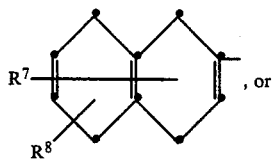, or

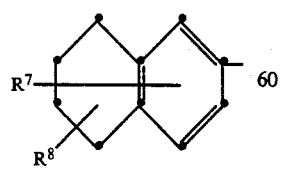

in which $R^7$ and $R^8$ independently are hydrogen, halo, hydroxy, $C_1$-$C_4$ alkyl, $C_1$-$C_4$ alkoxy, nitro, amino, $C_1$-$C_4$ alkanoylamino, $C_1$-$C_4$ alkylsulfonylamino, or when $R^7$ and $R^8$ are on adjacent carbon atoms, they can be taken together to form methylenedioxy;

A and B both are hydrogen, or taken together complete a double bond;

$R^2$ is hydrogen, an amino protecting group, hydroxy, or methoxy, and $R^3$ is hydrogen, or $R^2$ and $R^3$ taken together are

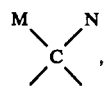

where M and N independently are $C_1$-$C_4$ alkyl;

$R^4$ is hydrogen, methoxy or methylthio;

$R^5$ is hydrogen, methoxy, methyl, halo, or methoxymethyl;

$R^6$ is hydrogen, a salt forming cation group, or a carboxy protecting group; and the pharmaceutically acceptable acid addition salts thereof; with the proviso that $R^2$ is hydroxy or methoxy only when A and B complete a double bond, and that A and B both are hydrogen when $R^3$ is other than hydrogen.

Preferred compounds provided by the invention include those of the above formula wherein
$R^1$ is

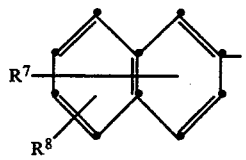

and $R^7$ and $R^8$ are as defined above. Within this group, preferred compounds include those wherein $R^2$ is hydrogen, an amino protecting group, hydroxy or methoxy, and $R^6$ is hydrogen or a carboxy protecting group.

Another preferred group of compounds are those wherein
$R^1$ is

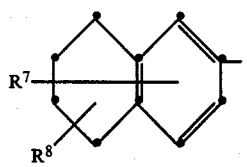

and $R^7$ and $R^8$ are as defined above. Especially preferred compounds within this group include those wherein A, B, $R^2$, $R^3$, $R^4$ and $R^6$ all are hydrogen.

A particularly preferred group of compounds provided by this invention are defined by the formula

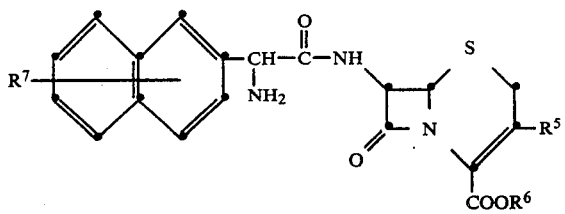

wherein $R^5$, $R^6$ and $R^7$ are as defined above. The most preferred compounds are those within this group wherein $R^7$ is hydrogen, halo, hydroxy or methoxy, $R^5$ is methyl or chloro, and $R^6$ is hydrogen or a salt forming group such as sodium or potassium cation.

An additional embodiment of this invention is a pharmaceutical formulation comprising a naphthylglycylamido cephalosporin derivative as defined above admixed with a pharmaceutical carrier, diluent or excipient therefor. A preferred formulation is one suitable for oral administration.

Yet another embodiment of this invention is a method for treating bacterial infections in animals comprising administering an effective amount of an antibacterial compound of the above formula. In a preferred method of treatment, the naphthylglycyl cephalosporin derivative is administered orally to treat diseases caused by gram positive microorganisms.

DETAILED DESCRIPTION OF THE INVENTION

In the above formula defining the compounds provided by this invention, $R^1$ defines a 2-naphthyl or 2-tetrahydronaphthyl group. The naphthyl and tetrahydronaphthyl groups may be unsubstituted, for instance when $R^7$ and $R^8$ both are hydrogen; mono-substituted at the 1, 3, 4, 5, 6, 7 or 8 positions, for instance when $R^8$ is hydrogen and $R^7$ is other than hydrogen; or disubstituted when $R^7$ and $R^8$ both are other than hydrogen. The groups with which the naphthyl and tetrahydronaphthyl rings may be substituted include hydroxy, $C_1$-$C_4$ alkyl, $C_1$-$C_4$ alkoxy, halo, nitro, amino, $C_1$-$C_4$ alkanoylamino and $C_1$-$C_4$ alkylsulfonylamino.

The term "$C_1$-$C_4$ alkyl" carries its art-recognized meaning of straight and branched lower alkyl carbon chains such as methyl, ethyl, isopropyl, n-propyl, isobutyl and tert.-butyl. Similarly, "$C_1$-$C_4$ alkoxy" refers to lower alkyl groups bonded to the naphthyl ring through an oxygen atom. Typical $C_1$-$C_4$ alkoxy groups include methoxy, ethoxy, n-propoxy, n-butoxy and isobutoxy. The term "halo" as used herein includes fluoro, chloro, bromo and iodo. A preferred halo group is chloro. "$C_1$-$C_4$ Alkanoylamino" refers to an acyl residue of a lower alkanoic acid, bonded to the naphthyl or tetrahydronaphthyl ring through a nitrogen atom. Such groups include formylamino, acetylamino and butyrylamino. "$C_1$-$C_4$ Alkylsulfonylamino" means a group such as methylsulfonylamino.

$R^2$ in the above formula defines a substituent on the glycyl nitrogen atom, and includes hydrogen and an amino protecting group. The term "amino protecting group" refers to any of the art-recognized substituents that can be attached to an amino nitrogen atom and which is readily removed when desired. Such protecting groups are often employed during preparation of the compounds of the invention, and serve to decrease the likelihood of unwanted side reactions occurring as a result of the presence of a free amino group. While the compounds wherein $R^2$ is a protecting group will have biological activity, it is contemplated that the most biologically desirable compounds will be those wherein $R^2$ is hydrogen. The compounds wherein $R^2$ is an amino protecting group are thus primarily useful as intermediates in the synthesis of the more preferred free amino compounds.

The precise nature of the amino protecting group is not critical to the invention, and any of the well known protecting groups can be employed. Typical amino protecting groups are described by J. W. Barton in "Protective Groups in Organic Chemistry," J. F. McOmie, Ed., Plenum Press, New York, N.Y., 1973, Chapter 2, and by Greene in "Protective Groups in Organic Synthesis", John Wiley & Sons, New York, N.Y., 1981, Chapter 7. Both of these references are incorporated herein by reference for their teaching of amino protecting groups.

The most common amino protecting groups to be employed include $C_1$-$C_{10}$ alkanoyl and halo $C_1$-$C_{10}$ alkanoyl groups such as formyl, acetyl, dichloroacetyl, propionyl, hexanoyl, 3,3-diethylhexanoyl, δ-chlorobutyryl, and the like; $C_1$-$C_{10}$ alkoxycarbonyl and $C_2$-$C_{10}$ alkenyloxycarbonyl groups such as methoxycarbonyl, tert.butoxycarbonyl, and allyloxycarbonyl; $C_5$-$C_{15}$ arylalkyl and arylalkenyloxycarbonyl such as benzyloxycarbonyl, 4-nitrobenzyloxycarbonyl and cinnamoyloxycarbonyl; halo-$C_1$-$C_{10}$ alkoxycarbonyl such as 2,2,2-trichloroethoxycarbonyl; and $C_5$-$C_{15}$-arylalkyl and alkenyl groups such as benzyl, phenethyl, trityl, allyl and the like.

Other commonly used amino protecting groups include enamines that are prepared by reaction of the free amino compound with a β-keto-ester such as methyl or ethyl acetoacetate.

In addition to representing hydrogen or an amino protecting group, $R^2$ in the above formula can be taken with $R^3$ to complete a ring system so as to form compounds of the formula

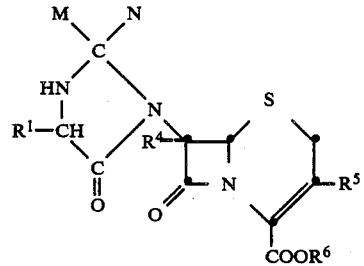

wherein $R^1$, $R^4$, $R^5$, $R^6$, M and N are as defined above. Exemplary of such compounds are the acetonides, those wherein M and N are both methyl. Such compounds are prepared by reacting a glycylamido cephalosporin wherein $R^2$ and $R^3$ both are hydrogen with a ketone such as acetone. These cyclic compounds are particularly useful as long-acting antibacterial agents.

$R^6$ in the above formula is hydrogen, a salt forming cation such as ammonium or an alkali metal cation such as lithium, sodium or potassium, or a carboxy protecting group. The term "carboxy protecting group" refers to the art-recognized groups commonly employed to block or protect the carboxylic acid functionality of a cephalosporin during chemical reactions involving other functional sites in the molecule, and which can be readily removed when desired by common hydrolytic or hydrogenolytic techniques. Typical carboxy protecting groups to be employed according to this invention include those described by E. Haslam in "Protective Groups in Organic Chemistry," supra, Chapter 5, and by Greene in "Protective Groups in Organic Synthesis," supra, Chapter 5, which are incorporated herein by reference. Examples of the commonly employed carboxy protecting groups include $C_1-C_{10}$ alkyl groups such as methyl, tert.-butyl, decyl; halo-$C_1-C_{10}$ alkyl such as 2,2,2-trichloroethyl, and 2-iodoethyl; $C_5-C_{15}$ arylalkyl such as benzyl, 4-methoxybenzyl, 4-nitrobenzyl, diphenylmethyl, triphenylmethyl; $C_1-C_{10}$ alkanoyloxymethyl such as acetoxymethyl, propionoxymethyl and the like; and groups such as phenacyl, 4-halophenacyl, allyl, dimethylallyl, tri($C_1-C_3$ alkyl)silyl such as trimethylsilyl, and related groups.

The naphthylglycyl and tetrahydronaphthylglycyl cephalosporins provided by this invention can be prepared by any of several methods, one of which comprises coupling a 7-aminocephalosporin nucleus of the formula

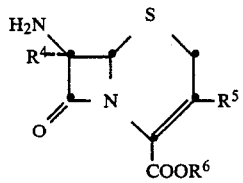

wherein $R^4$, $R^5$, and $R^6$ are as defined above, to a naphthylglycyl derivative of the formula

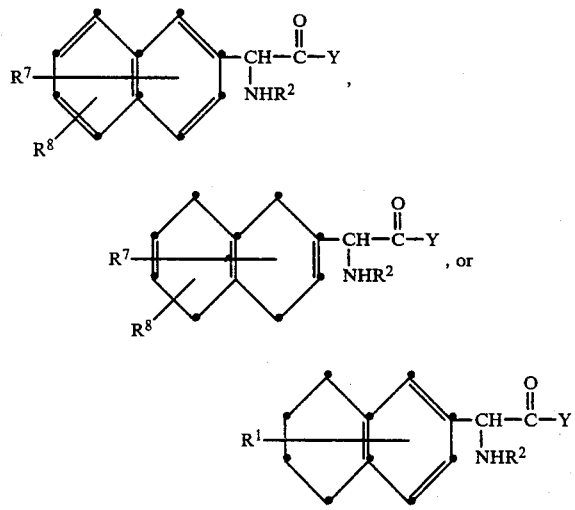

wherein $R^2$, $R^7$ and $R^8$ are as defined above, and Y is a leaving group such as hydroxy; halo, for instance chloro or bromo; or lower alkanoyloxy such as formyloxy or acetoxy. Examples of cephalosporin nuclei that can be employed in the synthesis of the compounds of this invention include those of the above formula wherein $R^4$, $R^7$ and $R^6$ have the following meanings:

| $R^4$ | $R^5$ | $R^6$ |
|---|---|---|
| H | —$CH_3$ | H |
| H | —$CH_3$ | tert.-butyl |
| $CH_3O$— | —$CH_3$ | p-nitrobenzyl |

| $R^4$ | $R^5$ | $R^6$ |
|---|---|---|
| H | —$CH_3$ | 2,2,2-trichloroethyl |
| H | —Cl | H |
| H | —Cl | tert.-butyl |
| H | —Cl | phenacyl |
| $CH_3S$ | —Cl | methyl |
| $CH_3O$ | H | H |
| H | H | p-nitrobenzyl |
| $CH_3S$ | —$CH_2OCH_3$ | diphenylmethyl |
| H | —$CH_2OCH_3$ | tert.-butyl |
| H | H | trimethylsilyl |
| H | —Cl | trityl |
| $CH_3O$— | —$H_3$ | tert.-butyl |
| H | —Br | H |
| H | —F | methyl |
| H | —$OCH_3$ | H |
| H | —$CH_3$ | p-nitrobenzyl |
| $CH_3S$— | —$CH_3$ | tert.-butyl |
| H | —Cl | allyl |
| H | —Br | 2,2,2-trichloroethyl |
| H | —I | methyl |

The 7-aminocephalosporin nuclei to be employed in the synthesis of compounds of this invention are well known in the art and are readily available by art known methods. For example, the 3-halo cephalosporin nuclei are available by the methods described in U.S. Pat. No. 3,925,372. 3-Methyl cephalosporin nuclei can be prepared by ring expansion of penicillin sulfoxides and subsequent side chain cleavage, or by hydrogenation of 3-acetoxymethyl derivatives.

Similarly, the naphthylglycyl and tetrahydronaphthylglycl reactants defined by the above formula are known in the art and are prepared employing procedures well known to organic chemists. Typical naphthylglycyl and tetrahydronaphthylglycyl derivatives that can be employed to prepare the compounds of the invention have the above formula wherein $R^2$, $R^7$, $R^8$ and Y have the following meanings:

| $R^7$ | $R^8$ | $R^2$ | Y |
|---|---|---|---|
| H | H | H | Cl hydrochloride |
| H | H | chloroacetyl | OH |
| H | 5-$OCH_3$ | allyloxycarbonyl | OH |
| H | 6-$OCH_3$ | tert.-butoxycarbonyl | Cl |
| H | 7-$OCH_3$ | benzyl | Br |
| H | 8-$OCH_2CH_3$ | trimethylsilyl | OCHO |
| 1-Cl | 5-$OCH_3$ | p-nitrobenzyl | $OCOCH_3$ |
| 3-Cl | 7-Cl | H | Br (hydrobromide) |
| 3-Cl | H | benzyloxycarbonyl | Br |
| 4-$OCH_3$ | | tert.-butoxycarbonyl | Cl |
| H | 7-$NO_2$ | methyl acetoacetate enamine | OH |
| 3-$NO_2$ | 8-I | 2,2,2-trichloroethoxycarbonyl | Cl |
| 7-$CH_2CH_2$ | 5-$CH_3$ | allyloxycarbonyl | OH |
| H | 6-$CH_3$ | formyl | Cl |
| H | 7-$CH_2CH_3$ | acetyl | OH |
| 1-OH | 8-$CH_2CH_2CH_3$ | benzoyl | HCHO |

The coupling of a naphthylglycyl or tetrahydronaphthylglycyl derivative with a 7-aminocephalosporin nucleus can be accomplished employing common techniques of acylation. For example, a naphthylglycyl acylating agent, wherein Y in the above formula is a leaving group such as halo, especially chloro or bromo, or alkanoyloxy such as formyloxy or acetoxy, can be reacted with a cephalosporin nucleus employing standard acylation conditions. During such acylation reaction, it generally is preferred that $R^2$ in the above formula be an amino protecting group and that $R^6$ be a carboxy protecting group. These protecting groups serve to minimize unwanted side reactions and to increase solubility characteristics of the respective reactants.

The acylation reaction generally is accomplished by combining approximately equimolar quantities of a naphthylglycyl or tetrahydronaphthylglycyl acylating agent (i.e. an acid halide or acid anhydride) with the 7-aminocephalosporin nucleus. The acylation reaction normally is carried out in a mutual solvent such as benzene, chloroform, dichloromethane, toluene, N,N-dimethylformamide, acetonitrile, or the like, and routinely is substantially complete after about 1 to about 12 hours when conducted at a temperature of about $-20°$ to about 60° C. About an equimolar quantity of a base such as pyridine, triethylamine, aniline, sodium carbonate or the like can be employed in the reaction if desired to act as an acid scavenger. The product may be isolated from the reaction mixture by simply removing the reaction solvent, for instance by evaporation under reduced pressure, and further purification can be accomplished if needed employing routine techniques such as chromatography, crystallization, solvent extraction, and related methods.

An alternative and preferred method for coupling a naphthylglycyl or tetrahydronaphthylglycyl derivative to a 7-aminocephalosporin nucleus to produce compounds of the invention employs a coupling reagent such as those routinely used in the synthesis of peptides. Typical coupling reagents that can be employed include carbodiimides such as N,N'-diethylcarbodiimide, N,N-diisopropylcarbodiimide, and N,N-dicyclohexylcarbodiimide (DCC); carbonyl coupling reagents such as carbonyldiimidazole; isoxazolinium salts such as N-ethyl-5'-phenylisoxazolinium-3'-sulfonate; and quinoline compounds such as N-ethoxycarbonyl-2-ethoxy-1,2-dihydroquinoline (EEDQ).

The coupling of a 7-aminocephalosporin nucleus with a naphthylglycyl or tetrahydronaphthylglycyl derivative employing a peptide coupling reagent generally is accomplished by combining approximately equimolar quantities of a 7-aminoceph-3-em-4-carboxylic acid derivative, a naphthylglycine derivative, and a peptide coupling reagent according to the following scheme;

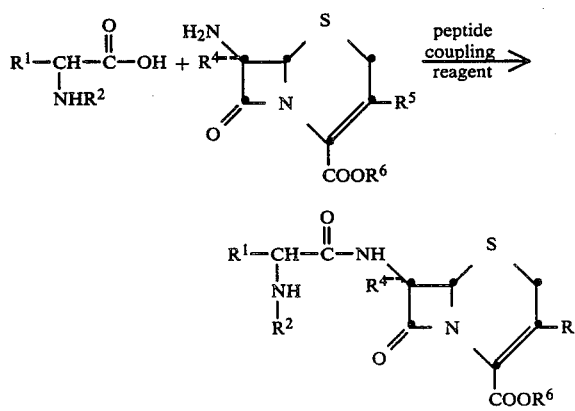

wherein $R^1$, $R^2$, $R^4$, $R^5$ and $R^6$ are as defined above. Preferably $R^2$ is an amino protecting group and $R^6$ is hydrogen or a carboxy protecting group during such coupling reactions. Any such protecting groups can be subsequently removed by standard methods to give the active antibiotic of the invention.

The coupling reaction normally is conducted in a mutual solvent such as dichloromethane, acetone, water, acetonitrile, N,N-dimethylformamide, chloroform, or the like, and routinely is substantially complete when carried out for about ten to about ninety minutes at a temperature of about $-20°$ to about 60° C. Longer reaction periods are not detrimental and can be employed if desired. The product, a naphthylglycyl or tetrahydronaphthylglycyl cephalosporin of the invention, is readily isolated by simply removing the reaction solvent, for instance by evaporation under reduced pressure. The product can be purified if needed by standard methods such as acid-base extraction, chromatography, salt formation or the like.

Still another method for preparing compounds of the invention employs a naphthyl oxime derivative of the formula

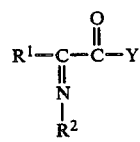

wherein $R^1$ and Y have the above-defined meanings, and $R^2$ is hydroxy or methoxy. When $R^2$ is hydroxy, it typically will be protected with a group such as trimethylsilyl or similar hydroxy protecting group. Such naphthyl oxime derivatives can be coupled to a cephalosporin nucleus by any of the methods described above to provide a compound of the formula

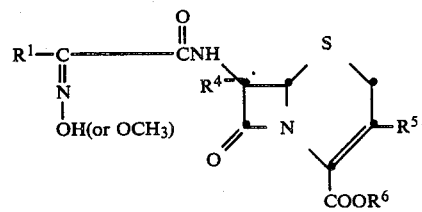

wherein $R^1$, $R^4$, $R^5$, and $R^6$ are as defined above. These compounds are useful as intermediates since they are readily reduced by normal methods to give the preferred glycyl compounds of the invention. Additionally, the oximes of the above formula wherein $R^6$ is hydrogen or a salt forming group are useful as antibiotics.

Yet another alternative method for preparing compounds of the invention comprises chemically modifying an intact naphthylglycyl or tetrahydronaphthylglycyl cephalosporin derivative. For example, a 3-exomethylene cephalosporin nucleus can be acylated with a naphthylglycyl derivative to form a naphthylglycyl 3-exomethylene cephalosporin. The latter compound can be converted by known methods to compounds of the invention. For instance, ozonolysis of a naphthylglycyl 3-exomethylene cephalosporin affords a 3-hydroxy compound, which upon halogenation affords the 3-halo naphthylglycyl and tetrahydronaphthylglycyl cephalosporins of the invention, while reaction with a base and a methylating agent affords the 3-methoxy compounds of the invention.

Compounds of the invention that bear a nitro group on the naphthylglycyl or the tetrahydronaphthylglycyl side chain can be modified to provide other compounds of the invention. For example, the nitro substituent can be reduced by routine reduction or hydrogenation procedures to give the corresponding amino substituted naphthylglycyl cephalosporin derivative, and if desired the amino group can be acylated by reaction with a $C_1$–$C_4$ alkanoyl halide or anhydride or a $C_1$–$C_4$ alkylsulfonyl halide to provide the corresponding alkanoylamino or alkylsulfonylamino naphthylglycylamido and tetrahydronaphthylglycylamido cephalosporins of the invention.

Similarly, compounds of the invention wherein $R^2$ and $R^3$ are taken together to form the group

are prepared by reacting a ketone of the formula

with a compound of the invention wherein $R^2$ and $R^3$ both are hydrogen, generally in the presence of an acid such as methanesulfonic acid or the like. The cyclic compounds thus produced, for instance the preferred acetonides wherein M and N both are methyl, are particularly useful as oral antibiotics since they are effective over prolonged periods of time.

Other compounds of the invention that are expected to be particularly long acting antibiotics are those wherein $R^2$ is an alkanoyl amino protecting group such as formyl or acetyl. Such compounds are conveniently prepared by simply reacting a naphthylglycylamido cephalosporin, wherein $R^2$ is hydrogen, with a $C_1$–$C_{10}$ alkanoyl acylating agent, for instance formyl chloride or acetic anhydride. These N-acylated products are expected to act not only as antibiotics in themselves, but also as pro-drugs in that they will be hydrolyzed in an animal system to the parent naphthylglycyl or tetrahydronaphthylglycyl derivative.

It should be noted that since the naphthylglycyl and tetrahydronaphthylglycyl side chains of the cephalosporins of this invention contain one asymmetric carbon atom, for example when A is hydrogen, the compounds of the invention can exist in the form of optical isomers, namely the D and the L isomers. The compounds of the invention can be employed as a DL-mixture to treat bacterial infections in animals, or if desired the optical isomers can be separated and employed individually. While both isomers are effective antibacterial agents, one isomer appears to be more potent than the other and is designated herein as the D-isomer, and accordingly is a preferred embodiment of the invention.

Separation or racemization of the optical isomers can be accomplished by routine methods carried out on the cephalosporin product of the invention or on the naphthylglycine or tetrahydronaphthylglycine side chain that is employed as a starting material. Separation of optical isomers generally will be accomplished by high performance chromatography, enzymatic resolution, or chemical crystallization or racemization. A particularly preferred method for obtaining D-naphthylglycine comprises reacting the D,L-mixture with benzaldehyde and optically active tartaric acid according to the method of U.S. Pat. No. 3,976,680.

As noted above, preferred compounds of the invention are those wherein $R^2$ in the above formula is hydrogen. Such compounds, being primary amines, are basic in nature and readily form pharmaceutically acceptable salts by reaction with acids. Typical acids commonly employed to form salts include inorganic acids such as hydrogen chloride, hydrogen bromide, sulfuric acid, phosphoric acid; as well as organic acids such as acetic acid, trifluoroacetic acid, succinic acid, methanesulfonic acid, oxalic acid, para-toluenesulfonic acid, and the like. The compounds of the invention wherein both $R^2$ and $R^6$ are hydrogen readily form an internal acid addition salt, namely a zwitterion.

The compounds of the invention generally exist as crystalline solids and can be crystallized from common solvents such as ethanol, water, N,N-dimethylformamide, acetone and the like. The compounds often crystallize as a solvate or hydrate and can be employed in such form.

Examples of typical classes of naphthylglycyl and tetrahydronaphthylglycyl cephalosporins, as well as specific compounds provided by this invention, include those listed below:

A. Preferred compounds of the formula

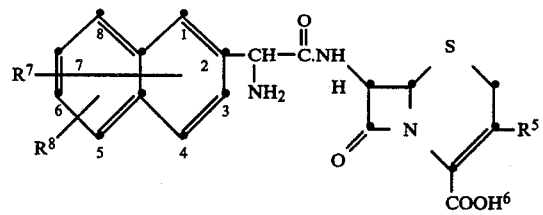

1. $R^6$ is hydrogen or a salt forming cation;
   a. $R^7$ and $R^8$ both are hydrogen;
      1a1. $R^5$ is methyl;
      1a2. $R^5$ is chloro;
      1a3. $R^5$ is bromo;
      1a4. $R^5$ is fluoro;
      1a5. $R^5$ is iodo;
      1a6. $R^5$ is hydrogen;
      1a7. $R^5$ is methoxy;
      1a8. $R^5$ is methoxymethyl;
   b. $R^7$ is hydrogen and $R^8$ is 6-methoxy;
      1b1. $R^5$ is methyl;
      1b2. $R^5$ is chloro;
      1b3. $R^5$ is methoxy;
      1b4. $R^5$ is methoxymethyl;
   c. $R^7$ is hydrogen and $R^8$ is 7-fluoro;
      1c1. $R^5$ is methyl;
      1c2. $R^5$ is chloro;
      1c3. $R^5$ is fluoro;
      1c4. $R^5$ is methoxy;
      1c5. $R^5$ is methoxymethy;
   d. $R^7$ is hydrogen and $R^8$ is 6-hydroxy;
      1d1. $R^5$ is methyl;
      1d2. $R^5$ is chloro;
      1d3. $R^5$ is methoxy;
      1d4. $R^5$ is bromo;
   e. $R^7$ is 4-methyl and $R^8$ is 6-chloro;
      1e1. $R^5$ is methyl;
      1e2. $R^5$ is methoxy;
      1e3. $R^5$ is chloro; and the acid addition salts thereof.

2. Those of the formula

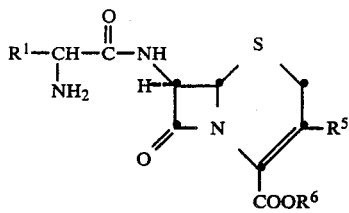

wherein $R^1$ is

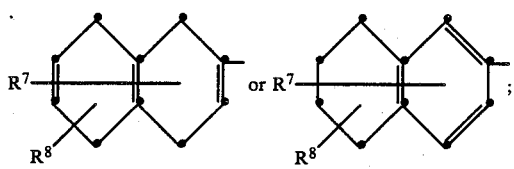

and $R^6$ is hydrogen or a salt forming cation.
  a. $R^7$ and $R^8$ both are hydrogen;
    2a1. $R^5$ is methyl;
    2a2. $R^5$ is chloro;
    2a3. $R^5$ is methoxy;
    2a4. $R^5$ is hydrogen;
  b. $R^7$ is hydrogen and $R^8$ is 7-hydroxy;
    2b1. $R^5$ is methyl;
    2b2. $R^5$ is fluoro;
    2b3. $R^5$ is iodo;
    2b4. $R^5$ is methoxy;
    2b5. $R^5$ is hydrogen;
  c. $R^7$ is 1-methoxy and $R^8$ is 8-tert.-butyl;
    2c1. $R^5$ is methyl;
    2c2. $R^5$ is methoxy;
    2c3. $R^5$ is chloro;
    2c4. $R^5$ is methoxymethyl;
  d. $R^7$ is 3-chloro and $R^8$ is 7-isopropoxy;
    2d1. $R^5$ is hydrogen;
    2d2. $R^5$ is methoxymethyl;
    2d3. $R^5$ is methoxy;
    2d4. $R^5$ is methyl;
    2d5. $R^5$ is chloro; and the acid addition salts thereof.

B. Those of the formula

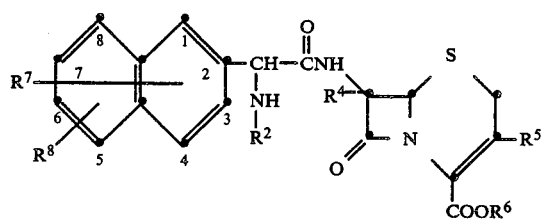

1. $R^4$ is hydrogen, $R^5$ is methyl;
  a. $R^7$ and $R^8$ both are hydrogen; $R^2$ is tert.-butoxycarbonyl;
    1a1. $R^6$ is p-nitrobenzyl;
    1a2. $R^6$ is 2,2,2-trichloroethyl;
    1a3. $R^6$ is trimethylsilyl;
    1a4. $R^6$ is phenacyl;
  b. $R^7$ and $R^8$ both are hydrogen, $R^6$ is tert.-butyl;
    1b1. $R^2$ is tert.-butoxycarbonyl;
    1b2. $R^2$ is acetyl;
    1b3. $R^2$ is p-nitrobenzyloxycarbonyl;
    1b4. $R^2$ is chloroacetyl;
  c. $R^7$ is hydrogen, $R^8$ is 7-methoxy, $R^2$ is 2,2,2-trichloroethoxycarbonyl;
    1c1. $R^6$ is p-nitrobenzyl;
    1c2. $R^6$ is sodium cation;
    1c3. $R^6$ is methyl;
2. $R^4$ is methoxy, $R^5$ is chloro;
  a. $R^7$ and $R^8$ both are hydrogen, $R^2$ is formyl;
    2a1. $R^6$ is 2,2,2-trichloroethyl;
    2a2. $R^6$ is hydrogen;
    2a3. $R^6$ is sodium cation;
3. $R^4$ is methylthio, $R^7$ and $R^8$ both are hydrogen;
  a. $R^5$ is methyl;
    3a1. $R^2$ is tert.-butoxycarbonyl;
    3a2. $R^6$ is para-nitrobenzyl;
  b. $R^5$ is bromo;
    3b1. $R^2$ is tert.-butoxycarbonyl;
    3b2. $R^6$ is trimethylsilyl;
  c. $R^5$ is methoxymethyl;
    3c1. $R^2$ is hydrogen;
    3c2. $R^2$ is trimethylsilyl;
    3c3. $R^6$ is allyl;
4. $R^4$ is methylthio, $R^7$ is hydrogen and $R^8$ is 6-methoxy;
  a. $R^5$ is methoxy;
    4a1. $R^2$ is tert-butoxycarbonyl;
    4a2. $R^6$ is methyl;
  b. $R^5$ is chloro;
    4b1. $R^2$ is hydrogen;
    4b2. $R^2$ is phenacyl;
    4b3. $R^6$ is tert.-butyl;

C. Those of the formula

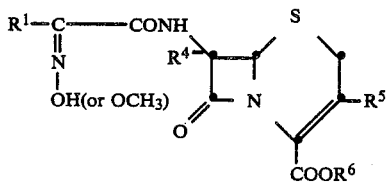

wherein $R^1$ is

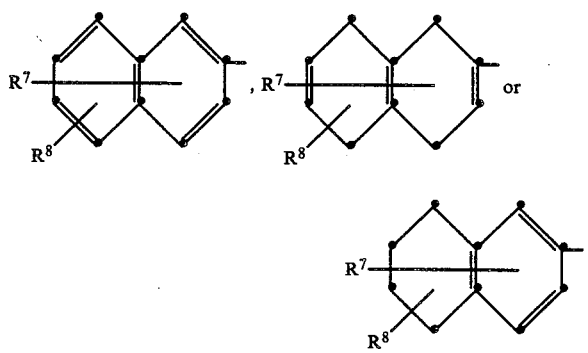

1. $R^7$ and $R^8$ both are hydrogen;
  a. $R^5$ is methyl;
    1a1. $R^6$ is para-nitrobenzyl;
    1a2. $R^6$ is tert.-butyl;
    1a3. $R^6$ is hydrogen;
    1a4. $R^6$ is trimethylsilyl;
  b. $R^5$ is fluoro;
    1b1. $R^6$ is methyl;
  c. $R^5$ is methoxymethyl;

The following detailed examples are provided by way of further illustration of the synthesis of compounds provided by the invention. The examples are not intended to limit the invention in any respect and should not be so construed.

PREPARATION 1

Preparation of 2-naphthylglycine (also named α-amino-α-(2-naphthyl)acetic acid)

A solution of 15.6 g (0.1 m) of 2-naphaldehyde in 700 ml of 50% ethanol-water containing 14.7 g (0.3 m) of sodium cyanide and 38.4 g (0.4 m) of ammonium carbonate was heated at 50° C. for twenty hours. The reaction mixture was cooled and concentrated to about 400 ml by evaporation under reduced pressure, and then the solution was made acidic to pH 2.0 by the addition of conc. hydrochloric acid. The solid precipitate that formed was collected by filtration, washed with dilute hydrochloric acid, and then dried to afford 22.1 g of 4-(2-naphthyl)-2,4-imidazolidindione.

A solution of 5.0 g (22 mM) of the 4-(2-naphthyl)-2,4-imidazolidindione in 100 ml of 16% (v/v) aqueous sodium hydroxide was heated at reflux for two and one-half hours. The reaction mixture was then filtered, cooled, and washed with ethylacetate. The aqueous solution was next diluted with 6N hydrochloric acid to pH 5.1 and filtered to provide 2-naphthylglycine. The reaction was repeated several times to produce larger quantities of the product.

A 10.0 g sample of 2-naphthylglycine was purified by dissolving it into 125 ml of methanol containing 3.9 ml of acetyl chloride. The reaction mixture was filtered and the filtrate was then diluted with 5 ml of aniline. The precipitated product was collected by filtration and dried to give 7.0 g of 2-naphthylglycine. m.p. 219°–221° C.

PREPARATION 2

Resolution of 2-naphthylglycine

A mixture of D and L 2-naphthylglycine was reacted with optically pure α-aminoethylbenzene in the presence of N,N'-dicyclohexylcarbodiimide to provide N-(1-phenylethyl)-α-amino-α-(2-naphthyl)acetamide. Separation of the diastereomers by chromatography over silica gel afforded, following acid hydrolysis, D-2-naphthylglycine (OR$-190°\pm3°$) and L-2-naphthylglycine (OR$=+190°\pm3°$).

PREPARATION 3

Preparation of 6-methoxynaphth-2-yl-glycine

2-Bromo-6-methoxynaphthalene was converted to the 2-lithio derivative by reaction with n-butyllithium. Diethyl oxalate was then reacted with the 2-lithio-6-methoxynaphthalene to afford ethyl α-keto-6-methoxynaphth-2-ylacetate. The latter compound was reacted with hydroxylamine hydrochloride and sodium acetate to provide ethyl α-hydroxyimino-6-methoxynaphth-2-ylacetate. A solution of 17.55 g of the oxime in 600 ml of methanol containing 5.3 g of zinc metal dust and 135 ml of 50% (v/v) aqueous formic acid was stirred at 0° C. for three hours. After filtering the reaction mixture, the solvent was removed by evaporation to give 10.3 g of ethyl α-amino-α-(6-methoxynaphth-2-yl)acetate.

NMR (CDCl$_3$): δ1.20 (t, 3H); δ2.15 (s, 2H); δ3.89 (s, 3H); δ4.15 (m, 1H); δ4.72 (s, 1H); δ6.08–6.75 (m, 6H).

Hydrolysis of the ester thus formed by reaction with 1N sodium hydroxide afforded 6-methoxynaphth-2-ylglycine.

PREPARATION 4

Preparation of N-tert.-butoxycarbonyl-2-naphthylglycine

To a stirred solution of 10 g (50 mM) of 2-naphthylglycine (from Preparation 1) in 100 ml of 1N sodium hydroxide were added 50 ml of tetrahydrofuran followed by 30 g (140 mM) of di-tert.-butyl carbonate. The reaction mixture was stirred at 24° C. for four hours. The product was isolated by first washing the reaction mixture three times with 50 ml portions of diethyl ether, and then the mixture was made acidic to pH 2.0 by the addition of conc. hydrochloric acid. The aqueous acid mixture was extracted several times with ethyl acetate, and the extracts were combined, washed with water, dried and the solvent was removed by evaporation under reduced pressure to provide 12.8 g (85% yield) of N-tert.-butoxycarbonyl-2-naphthylglycine.

NMR (DMSO): δ2.5 (s, 9H); δ6.85 (s, 1H); δ7.28–7.9 (m, 7H).

By following the general procedures set out in Preparations 1–4 the following compounds were prepared:

N-tert.-butoxycarbonyl-(6-methoxy-2-naphthyl)glycine NMR (CDCl$_3$):δ1.2 and 1.4 (two broad singlets, 9H); δ5.4 (broad singlet, 1H); δ6.7 (broad singlet, 1H); δ7.03–7.8 (m, 6H).

N-tert.-butoxycarbonyl-(6-hydroxy-2-naphthyl)glycine NMR (CDCl$_3$) δ1.2–1.4 (broad singlet, 9H); δ5.3–5.9 (two broad singlets, 1H); δ6.9–8.5 (m, 7H).

N-tert.-butoxycarbonyl-(6-chloro-2-naphthyl)glycine NMR (DCDl$_3$) δ1.15 (s, 9H); δ5.3–5.7 (m, 1H); δ7.3–8.3 (m, 8H).

PREPARATION 5

α-Amino-α-(2-naphthyl)acetyl chloride hydrochloride

Hydrogen chloride was bubbled through a cold (0° C.) solution of 5.0 g (25 mM) of 2-naphthylglycine in 150 ml of dichloromethane for twenty minutes. The reaction mixture was then stirred while 7.6 g (38 mM) of phosphorus pentachloride were added in one portion, and stirring was continued at 0°–10° C. for two hours. The solution was filtered, dried, and the solvent was removed by evaporation under reduced pressure to give 5.2 g (81% yield) of α-amino-α-(2-naphthyl)acetyl chloride hydrochloride. IR (mull) 1795 cm$^{-1}$ Analysis calculated for C$_{12}$H$_{11}$Cl$_2$NO: Theory: Cl, 27.68. Found: Cl, 27.69.

PREPARATION 6

Enzymatic resolution of D,L 2-naphthylglycine

By following the general procedure of U.S. Pat. No. 3,386,888, 19.8 g of D,L-N-chloroacetyl-2-naphthylglycine was reacted with 4 g of N-acyl L-amino acid amidohydrolase in 1250 ml of 0.1M potassium hydrogen phosphate pH 7.0 buffer containing $5\times10^{-4}$M cobalt chloride hexahydrate. The reaction mixture was shaken for two hours at 37° C. L-2-Naphthylglycine had precipitated and was removed by filtration. The filtrate was acidified to pH 2 by addition of 1N hydrochloric acid, and the mixture was extracted twice with 500 ml portions of ethyl acetate. The extracts were combined, dried, and the solvent was removed by evaporation under reduced pressure to give 9.065 g of D-N-chloroacetyl-2-naphthylglycine (91.5% yield).

Analysis calc. for $C_{14}H_{12}NO_3Cl$: Theory: C, 60.55; H, 4.36; N, 5.04. Found: C, 60.62; H, 4.34; N, 4.76. $[\alpha_D^{25}] -212.0°$ The L-2-naphthylglycine that was collected by filtration was washed with pH 7.0 buffer, with water, and finally with hexane and air dried to give 6.82 g (95% yield) of L-2-naphthylglycine.

Analysis calc. for $C_{12}H_{11}NO_2$: Theory: C, 71.63; H, 5.55; N, 6.96. Found: C, 69.85; H, 5.62; N, 6.51. $[\alpha_D^{25}]+195.2°$.

PREPARATION 7

8-Nitro-2-napthoic acid

5-Nitro-2-napthoic acid

To a stirred solution of 400 ml concentrated nitric acid at 60° C. were added portion-wise 18 g (0.11 M) of 2-napthoic. The reaction mixture was heated at 70° C. for two hours, cooled, and added to 200 g of ice. The precipitate was collected by filtration and dried to give 18.8 g (77% yield) of a mixture of 5 and 8-nitro-2-napthoic acid. The mixture was converted to the ethyl ester by reaction with ethanol in the presence of sulfuric acid. Five grams of the mixture of ethyl esters were crystallized from 20 ml of ethyl acetate to give 800 mg of ethyl 8-nitro-2-napthoate (m.p. 120° C.) and 1.9 g of ethyl 5-nitro-2-napthoate.

PREPARATION 8

Ethyl 8-Amino-2-naphthylformate

A solution of 11.2 g of ethyl 8-amino-2-napthoate (prepared as in Preparation 7) in 100 ml of ethanol was hydrogenated in the presence of 5% palladium on carbon. The reaction mixture was filtered and the solvent was removed from the filtrate to give ethyl 8-amino-2-naphthylformate.

PREPARATION 9

Ethyl 8-hydroxy-2-naphthylformate

To a cold (0° C.) stirred solution of 9.5 g (44 mM) of ethyl 8-amino-2-naphthylformate in 150 ml of 6N sulfuric acid was added dropwise over ten minutes a solution of 3.1 g (45 mM) of sodium nitrite in 25 ml of water. The reaction mixture was stirred for fifty minutes and then added to a hot solution (90° C.) of 90 ml of water in 10 ml of conc. sulfuric acid. The reaction mixture was stirred for ten minutes at 90° C., then cooled and extracted with dichloromethane. The extracts were combined, washed with brine, dried, and the solvent was removed to give, following purification by chromatography, 1.7 g of ethyl 8-hydroxy-2-naphthylformate. m.p. 136°-137° C.

Following the same general procedure, 14.9 g of ethyl 8-amino-2-naphthylformate were reacted with tert.-butyl nitrite and copper (11) chloride to give 11.5 g of ethyl 8-chloro-2-naphthylformate.

PREPARATION 10

Ethyl 8-methoxy-2-naphthylformate

A solution of 216 mg of ethyl 8-hydroxy-2-naphthylformate (from Preparation 9) in 15 ml of acetone containing six drops of dimethyl sulfate and 150 mg of potassium carbonate was stirred at 25° C. for twenty-four hours. The reaction solvent was removed and the product was dissolved in ethyl acetate, washed with 5% hydrochloric acid and with brine, dried and concentrated to give 200 mg of ethyl 8-methoxy-2-naphthylformate.

PREPARATION 11

α-Methoxyimino-α-(8-chloro-2-naphthyl)acetic acid

A suspension of 9.2 g sodium hydride in 50 ml of N,N-dimethylformamide was added in one portion to a stirred solution of 5.6 g (24 mM) of ethyl 8-chloro-2-naphthylformate and 4.4 g (36 mM) of methyl methylthiomethyl sulfoxide in 10 ml of N,N-dimethylformamide. The reaction mixture was stirred for four hours at 25° C., and then concentrated to dryness. The product was dissolved in 250 ml of ethyl acetate and the solution was washed with 5% hydrochloric acid, saturated sodium bicarbonate and brine. The solution was dried and the solvent was removed by evaporation to give 4.73 g (63% yield) of 1-oxo-1-(8-chloro-2-naphthyl)-2-methylthio-2-methylsulfinylethane. A solution of 3.12 g (10 mM) of the product in 150 ml of formic acid and 12 ml of acetic anhydride was stirred at 65° C. for thirty minutes. To the reaction mixture were added 856 mg (4 mM) of sodium periodate and stirring was continued for an additional fifteen minutes. The reaction mixture was cooled and concentrated to dryness, and the product was dissolved in ethyl acetate, washed with sodium bicarbonate and brine, and the solvent was removed to give 1.2 g (46% yield) of methylthio α-oxo-α-(8-chloro-2-naphthyl)acetate.

A solution of 220 mg of the product from above in 15 ml of methanol and 15 ml of water containing 0.83 ml of 1N sodium hydroxide and 70 mg of methoxyamine hydrochloride was stirred for sixteen hours at 25° C. The reaction mixture was made acid to pH 2 by addition of 1N hydrochloric acid. The acid solution was extracted with ethyl acetate which was dried and concentrated to give 170 mg of α-methoxyimino-α-(8-chloro-2-naphthyl)acetic acid.

By following the same general procedure, the following compounds are prepared:

α-Methoxyimino-α-(8-nitro-2-naphthyl)acetic acid;
α-Methoxyimino-α-(8-amino-2-naphthyl)acetic acid;
α-Methoxyimino-α-(8-hydroxy-2-naphthyl)acetic acid; and
α-Methoxyimino-α-(8-methoxy-2-naphthyl)acetic acid.

PREPARATION 12

Preparation of 7-amino-3-chloro-3-cephem-4-carboxylic acid

U.S. Pat. No. 3,925,372 describes the synthesis of 7-phenylglycylamido-3-chloro-3-cephem-4-carboxylic acid, now generically known as cefaclor. Reaction of cefaclor with phosphorous pentachloride, methanol and water under known conditions for cleavage of cephalosporin side chains affords 7-amino-3-chloro-3-cephem-4-carboxylic acid.

Similarly prepared are the following nuclei that can be employed in the synthesis of compounds of the present invention:

7-amino-7-methoxy-3-bromo-3-cephem-4-carboxylic acid;
7-amino-3-cephem-4-carboxylic acid;
7-amino-3-methoxymethyl-3-cephem-4-carboxylic acid;
7-amino-7-methylthio-3-methyl-3-cephem-4-carboxylic acid;

EXAMPLE 1

7-(2-Naphthylglycylamido)-3-methyl-3-cephem-4-carboxylic acid trifluoroacetate salt To a stirred suspension of 1.0 g (4.7 mM) of 7amino-3-methyl-3-cephem-4-carboxylic acid (7-ADCA) in 25 ml of acetonitrile were added in one portion 3.7 ml (14.0 mM) of bis(trimethylsilyl)trifluoroacetamide. The reaction mixture was stirred at room temperature until all solids had dissolved, thus indicating complete formation of the trimethylsilyl ester of 7-ADCA.

In a separate flask a solution of 1.35 g (4.5 mM) of N-tert.-butoxycarbonyl-2-naphthylglycine (from Preparation 4) in 20 ml of acetonitrile containing 1.1 g (4.5 mM) of N-ethoxycarbonyl-2-ethoxy-1,2-dihydroquinoline (EEDQ) was stirred at room temperature for fifteen minutes. This solution was then added in one portion to the cold (0° C.) acetonitrile solution containing the trimethylsilyl ester of 7-ADCA from above. The reaction mixture was stirred for one hour at 0° C., and then warmed to room temperature. The solvent was removed by evaporation under reduced pressure to give an oil, and the oil was dissolved in ethyl acetate, washed two times with 1N hydrochloric acid, dried, and the solvent was removed by evaporation to provide 7-(N-tert.-butoxycarbonyl-2-naphthylglycylamido)-3-methyl-3-cephem-4-carboxylic acid as a foam.

The N-protected naphthylglycyl cephalosporin thus produced was dissolved in 5 ml of trifluoroacetic acid, and then the trifluoroacetic acid was removed by evaporation under reduced pressure to provide, following precipitation from diethyl ether, 5.7 g of 7-(2-naphthylglycylamido)-3-methyl-3-cephem-4-carboxylic acid trifluoroacetate salt.

EXAMPLE 2

7-(2-Naphthylglycylamido)-3-methyl-3-cephem-4-carboxylic acid

A mixture of 5.7 g of the trifluoroacetic acid addition salt from Example 1 in 55 ml of 10% (v/v) water and acetonitrile was warmed to about 50° C. and then filtered to remove the undissolved solids. The filtrate was then diluted with 1.8 molar ammonium hydroxide to pH 4.5. The precipitate that formed was collected by filtration and dried to give 3.15 g (72% yield) of 7-(2-naphthylglycylamido)-3-methyl-3-cephem-4-carboxylic acid.

EXAMPLE 3

The procedure of Example 1 was repeated using 5.0 g of optically active D-N-tert.-butoxycarbonyl-2-naphthylglycine and 5.6 g of 7-ADCA to provide, following removal of the N-protecting group, 6.8 g (80% yield) of D-7-(2-naphthylglycylamido)-3-methyl-3-cephem-4-carboxylic acid trifluoroacetic acid salt. The salt thus formed was dissolved in 90 ml of acetonitrile and 10 ml of water containing 5 ml of triethylamine. The reaction mixture was stirred at 25° C. for twenty minutes and filtered. The filtrate was concentrated to dryness and the product was crystallized from water to give 2.9 g of D-7-(2-naphthylglycylamido)-3-methyl-3-cephem-4-carboxylic acid tetrahydrate. m.p. 171°–180° C. (dec.)

Analysis calc. for $C_{20}H_{27}N_3O_8S$: Theory: C, 51.16; H, 5.80; N, 8.95; S, 6.93. Found: C, 52.52; H, 5.47; N, 8.73; S, 6.83.

NMR (DMSOd$_6$) δ1.9 (s, 3H); δ4.8 (s, 1H); δ4.9 (dd, 1H); δ5.6 (dd, 1H); δ7.49–7.99 (m, 7H).

EXAMPLE 4 p-Nitrobenzyl 7-(N-tert.-butoxycarbonyl-2-naphthylglycylamido)-3-chloro-3-cephem-4-carboxylate A solution of 260 mg of EEDQ in 50 ml of acetonitrile containing 301 mg of N-tert.-butoxycarbonyl-2-naphthylglycine was added in one portion to a stirred cold (0° C.) solution of 682 mg of p-nitrobenzyl 7-amino-3-chloro-3-cephem-4-carboxylate in 50 ml of acetonitrile. The reaction mixture was stirred for ninety minutes at 0° C., and then was warmed to room temperature. The reaction solvent was removed by evaporation under reduced pressure to provide the product as an oil. The oil was dissolved in ethyl acetate and washed with dilute hydrochloric acid, pH 7.0 buffer, and finally with brine. After drying the organic solution, the solvent was removed by evaporation to provide 598 mg (93% yield) of p-nitrobenzyl 7-(N-tert.-butoxycarbonyl-2-naphthylglycylamido)-3-chloro-3-cephem-4-carboxylate.

NMR (CDCl3) δ1.21 (s, 9H); δ3.1–3.8 (m, 2H); δ4.9 (two doublets, 1H); δ5.28 (s, 2H); δ5.4–6.2 (m, 3H); δ7.2–8.21 (m, 12H).

EXAMPLE 5

7-(2-Naphthylglycylamido)-3-chloro-3-cephem-4carboxylic acid trifluoroacetate

To a solution of 598 mg of p-nitrobenzyl 7-(N-tert.-butoxycarbonyl-2-naphthylglycylamido)-3-chloro-3-cephem-4-carboxylate (from Example 4) in 50 ml of tetrahydrofuran containing 10 ml of methanol and 5 ml of ethanol were added portionwise 1.20 g of 5% palladium on carbon. The reaction mixture was shaken for one hour in a Paar hydrogenation flask under an initial hydrogen pressure of 58 psi. The reaction mixture was then filtered and the solvent was removed from the filtrate by evaporation under reduced pressure to provide an oil. The oil was dissolved in pH 7.0 buffer, and the pH was adjusted to 7.75 by addition of dilute sodium hydroxide. The aqueous solution was washed with ethyl acetate and diethyl ether, and then acidified to pH 2.3 by addition of 1N hydrochloric acid. The acidic solution was extracted with ethyl acetate, which was then dried and the solvent was removed by evaporation to provide 360 mg (77% yield) of 7-(N-tert.-butoxycarbonyl-2-naphthylglycylamido)-3-chloro-3-cephem-4-carboxylic acid.

The acid thus produced was dissolved in 6 ml of trifluoroacetic acid and the solution was stirred for five minutes at 25° C. The pH was then adjusted to 3.9 by addition of dilute ammonium hydroxide, and the solvents were removed by evaporation to provide an oil. The oil was subjected to gradient chromatography over reverse phase silica gel, eluting with 0–25% acetonitrile, 1% acetic acid and 99–74% water (v/v). The appropriate fractions were combined and the solvent was removed by lyopholyzation to afford 49 mg of L- and 49 mg of D-7-(2-naphthylglycylamido)-3-chloro-3-cephem-4-carboxylic acid.

NMR (TFA$_d$1) δ3.82 (q, 2H); δ5.49 (d, 1H); δ5.8–6.1 (m, 2H); δ7.6–8.35 (m, 7H).

EXAMPLE 6

7-(2-Naphthylglycylamido)-3-methoxy-3-cephem-4-carboxylic acid trifluoroacetate A solution of 1.05 g of D,L-N-tert.-butoxycarbonyl 2-naphthylglycine in 15 ml of acetonitrile containing 1.06 g of EEDQ was stirred at 25° C. for thirty minutes, and then was added in one portion to a stirred solution of 1.0 g of 7-amino-3-methoxy-3-cephem-4-carboxylic acid in 15 ml of acetonitrile containing 1 ml of bis(trimethylsilyl)trifluoroacetamide. The reaction mixture was stirred for two hours at 25° C. and then concentrated to dryness by evaporation of the solvent under reduced pressure to provide an oil. The oil was dissolved in 10 ml of trifluoroacetic acid and stored at 0° C. for five minutes. Evaporation of the solvent and purification of the product by chromatography over silica gel afforded 89.5 mg of D,L 7-(2-naphthylglycylamido)-3-methoxy-3-cephem-4-carboxylic acid trifluoroacetate.

IR (KBr): 1762.10 cm$^{-1}$ ($\beta$-lactam); NMR (TFA$_d$1) $\delta$3.2–4.25 (m, 5H); $\delta$5.2–5.9 (m, 3H); $\delta$7.5–8.3 (m, 7H).

EXAMPLE 7

D-7-(6-chloronaphth-2-ylglycylamido)-3-methyl-3-cephem-4-carboxylic acid

2-Chloronaphthalene was acylated with ethyl chlorooxalyate to produce ethyl $\alpha$-keto-$\alpha$-(6-chloronaphth-2-yl)acetic acid. Reaction of the latter compound with hydroxylamine, followed by reduction and hydrolysis, provided 6-chloronaphth-2-ylglycine. This was converted to the N-tert.-butoxycarbonyl protected derivative.

To a stirred cold (0° C.) solution of 523 mg (1.5 mM) of p-nitrobenzyl 7-amino-3-methyl-3-cephem-4-carboxylate in 300 ml of acetonitrile was added a solution of 500 mg (1.5 mM) of N-tert.-butoxycarbonyl-6-chloronaphth-2-ylglycine in 100 ml of acetonitrile containing 369 mg of EEDQ. The reaction mixture was stirred for one hour at 0° C., and then was warmed to room temperature and stirred for an additional forty-eight hours. The reaction solvent was next removed by evaporation under reduced pressure to provide the product as an oil. The oil was dissolved in 100 ml of ethyl acetate and washed with 1N hydrochloric acid, aqueous sodium bicarbonate, water, and then dried. Removal of the solvent by evaporation afforded 770 mg of a white solid (77% yield) of p-nitrobenzyl 7-(N-tert.-butoxycarbonyl-6-chloronaphth-2-ylglycylamido)-3-methyl-3-cephem-4-carboxylate.

NMR (CDCl3) $\delta$1.40 (s, 9H); $\delta$2.12 (two singlets, 3H); $\delta$3.40 (q, 2H); $\delta$4.68 and 4.90 (two doublets, 1H); $\delta$5.30 (broad s, 3H); $\delta$5.6–6.0 (m, 1H); $\delta$7.2–8.3 (m, 8H).

Removal of the p-nitrobenzyl carboxy protecting group was accomplished by hydrogenation of 770 mg of the compound from above with 1.0 g of 5% palladium on carbon in 50 ml of methanol containing 20 ml of ethanol with an initial hydrogen pressure of 55 psi. The reaction was complete after fifty-five minutes, and the reaction mixture was filtered and the solvent was removed from the filtrate to give an oil. The oil was dissolved in 50 ml of ethyl acetate containing pH 7 buffer, and the aqueous layer was acidified to pH 2.3 with 1N hydrochloric acid. The product was extracted into ethyl acetate, which was then washed with water, dried and concentrated to dryness to afford 220 mg (36% yield) of 7-(N-tert.-butoxycarbonyl-6-chloronaphth-2-ylglycylamido)-3-methyl-3-cephem-4-carboxylic acid.

NMR (CDCl3) $\delta$1.46 (s, 9H); 2.15 (two singlets, 3H); $\delta$3.35 (m, 2H); $\delta$7.2–8.1 (m, 8H).

The product thus formed was dissolved in 5 ml of trifluoroacetic acid and the solution was stirred at room temperature for five minutes. Evaporation of the solvent and purification of the product by high pressure liquid chromatography provided D-7-(6-chloronaphth-2-ylglycylamido)-3-methyl-3-cephem-4-carboxylic acid.

EXAMPLE 8

7-(2-Naphthylglycylamido)-3-methoxymethyl-3-cephem-4-carboxylic acid

A solution of 570 mg of diphenylmethyl 7-amino-3-methoxymethyl-3-cephem-4-carboxylate tosylate in 30 ml of ethylacetate containing 10 ml of aqueous sodium bicarbonate was stirred for five minutes and then concentrated to dryness to give diphenylmethyl 7-amino-3-methoxymethyl-3-cephem-4-carboxylate as a white foam. The foam was dissolved in 20 ml of acetonitrile and added in one portion to a stirred solution of 301 mg of D-N-tert.-butoxycarbonyl-2-naphthylglycine in 20 ml of acetonitrile containing 207 mg of N,N$^1$-dicyclohexylcarbodiimide and 135 mg of hydroxybenzotriazole. The reaction mixture was stirred at 25° C. for four hours. The mixture was poured into 100 ml of ethyl acetate and the solution was washed once with 50 ml of aqueous sodium bicarbonate, once with 50 ml of 1N hydrochloric acid, once with water, dried, and the solvent was removed by evaporation under reduced pressure to give diphenylmethyl D-7-(N-tert.-butoxycarbonyl-2-naphthylglycylamido)-3-methoxymethyl-3-cephem-4-carboxylate as a white foam. The foam was dissolved in 2 ml of triethylsilane and 5 ml of trifluoroacetic acid and the solution was stirred at 25° C. for nine minutes. Removal of the solvent by evaporation under reduced pressure provided 260 mg of D-7-(2-naphthylglycylamido)-3-methoxymethyl-3-cephem-4-carboxylic acid trifluoroacetate salt.

The salt thus formed was dissolved in 5 ml of water and 5 ml of acetonitrile and the pH of the mixture was adjusted to 4.5 with 1N ammonium hydroxide. The solution was lyophilized to provide a white solid, which when purified by preparative reverse phase high pressure liquid chromatography afforded 20 mg of D-7-(2-naphthylglycylamido)-3-methoxymethyl-3-cephem-4carboxylate.

NMR (DMSOd6) $\delta$3.13 (s, 3H); $\delta$3.28 (q, 2H); $\delta$4.12 (s, 2H); $\delta$4.95 (d, 1H); $\delta$5.65 (d, 1H); $\delta$7.41–4.23 (m, 7H).

EXAMPLE 9 p-Nitrobenzyl 9-[N-tert. butoxycarbonyl-(6-methoxy-2-naphthyl)glycylamido]-3-methyl-3-cephem-4-carboxylate To a stirred solution of 662 mg (2 mM) of N-tert.-butoxycarbonyl-(6-methoxy-2-naphthyl)glycine in 100 ml of acetonitrile containing 500 mg (2 mM) of N-ethoxycarbonyl-2-ethoxy-1,2-dihydroquinoline were added in one portion 770 mg (2.2 mM) of p-nitrobenzyl 7-amino-3-methyl-3-cephem-4-carboxylate. The reaction mixture was stirred at 25° C. for sixteen hours and then concentrated to dryness to provide an oil. The oil was dissolved in 50 ml of ethyl acetate and the solution was washed with 25 ml of 1N hydrochloric acid, 25 ml of aqueous sodium bicarbonate and water. The solution was dried and concentrated to dryness to provide 1.3 g of p-nitrobenzyl 7-[N-tert.-butoxycarbonyl-(6-methoxy- 2-naphthyl)glycylamido]-3-methyl-3-cephem-4-carboxylate.

NMR (CDCl3) δ1.39 (s, 9H); δ2.08 and 2.15 (two singlets, 3H); δ3.34 (q, 2H); δ3.90 (s, 3H); δ4.9 (m, 1H); δ5.29 (s, 2H); δ5.31 (s, 1H); δ5.68 (m, 1H); δ7.08–8.25 (m, 12).

EXAMPLE 10

D-7-(6-Methoxy-2-naphthyl)glycylamido-3-methyl-3-cephem-4-carboxylic acid

To a stirred suspension of 1.4 g of 5% palladium on carbon in 50 ml of ethanol were added in one portion 1.3 g of p-nitrobenzyl 7-[N-tert.-butoxycarbonyl-(6-methoxy-2-naphthyl)glycylamido]-3-methyl-3-cephem-4-carboxylate. The reaction mixture was stirred for three hours at 25° C. under 55 psi hydrogen. The reaction mixture was then filtered and the filter cake was washed with fresh ethanol. The filtrate was concentrated to dryness by evaporation under reduced pressure to provide 1.1 g of 7-[N-tert.-butoxycarbonyl-(6-methoxy-2-naphthyl)glycylamido]-3-methyl-3-cephem-4-carboxylic acid.

The acid thus formed was dissolved in 5 ml of trifluoroacetic acid and the solution was stirred at 25° C. for five minutes. The reaction mixture was added to 20 ml of water and the aqueous solution was lyophilized for twelve hours to give D,L-7-(6-methoxy-2-naphthylglycylamido)-3-methyl-3-cephem-4-carboxylic acid trifluoroacetate. The salt thus formed was re-dissolved in fresh water and purified by high performance liquid chromatography to afford D-7-(6-methoxy-2-naphthylglycylamido)-3-methyl-3-cephem-4-carboxylic acid.

NMR (TFA$_d$1) δ2.42 (s, 3H); δ3.50 (q, 2H); δ4.30 s, 3H); δ5.39 (d, 1H); δ5.8–6.1 (m, 2H); δ7.42–8.30 (m, 6H).

Example 11

Following the general procedure of Examples 9 and 10 p-nitrobenzyl 7-amino-3-methyl-3-cephem-4-carboxylate was reacted with D,L-N-tert.-butoxycarbonyl-(6-hydroxy-2-naphthyl)glycine in the presence of EEDQ to provide p-nitrobenzyl D,L-7-[N-tert.-butoxycarbonyl-(6-hydroxy-2-naphthyl)glycylamido]-3-methyl-3-cephem-4-carboxylate.

NMR (CDCL3) δ1.41 (s, 9H); δ2.02 and 2.10 (two singlets, 3H); δ2.9–3.5 (m, 2H); δ4.9 (m, 1H); δ5.23 (s, 2H); δ5.35 (m, 1H); δ5.6–6.0 (m, 2H); δ6.72–8.21 (m, 12H). The compound thus prepared was reacted with hydrogen and 5% palladium on carbon to give D,L-7-[N-tert.-butoxycarbonyl-(6-hydroxy-2-naphthyl)-glycylamido]-3methyl-3-cephem-4-carboxylic acid.

NMR (CDCL3) δ1.15 (s, 9H); δ1.82 and 1.89 (two singlets, 3H); δ4.65 (two doublets, 1H); δ5.23 (m, 1H); δ6.0 (m, 1H); δ6.7–7.9 (m, 7H); δ8.5 (m, 2H). Reaction of the compound from above with trifluoroacetic acid afforded D,L 7-(6-hydroxy-2-naphthylglycylamido)-3-methyl-3-cephem-4-carboxylic acid. The isomers were separated by high performance liquid chromatography to give D-7-(6-hydroxy-2-naphthylglycyl- amido)-3-methyl-3-cephem-4-carboxylic acid.

EXAMPLE 12

D-7-(2-Naphthylglycylamido)-3-cephem-4-carboxylic acid trifluoroacetate

To a stirred suspension of 2.0 g (10 mM) of 7-amino-3-cephem-4-carboxylic acid in 15 ml of acetonitrile were added in one portion 8 ml (30 mM) of bis(trimethylsilyl)trifluoroacetamide. The mixture was stirred at 25° C. for thirty minutes, and then was cooled to 0° C. and added in one portion to a stirred solution of 2.0 g (6.6 mM) of D,L-N-tert.-butoxycarbonyl-2-naphthylglycine in 15 ml of acetonitrile containing 1.73 g (7.0 mM) of EEDQ. The reaction mixture was stirred for one hour at 25° C. and then was concentrated to dryness to provide an oil. The oil was dissolved in 100 ml of ethyl acetate and washed four times with 25 ml portions of 1N hydrochloric acid, twice with brine, and dried. The solvent was removed by evaporation under reduced pressure to provide a white foam. The foam was dissolved in 25 ml of trifluoroacetic acid and the solution was sonicated for five minutes at 25° C. The reaction mxiture was concentrated to dryness and triturated with diethyl ether to afford 1.8 g (55% yield) of D,L-7-(2-naphthylglycylamido)-3-cephem-4-carboxylic acid trifluoroacetate. The product thus produced was chromatographed over reverse phase C$_{18}$ silica gel, eluting with 8 liters of a solution of 1% acetic acid plus a gradient of 95% water −5% acetonitrile to 85% water −15% acetonitrile (v/v). The appropriate fractions were combined and the solvent was removed by lyophilization to afford 157 mg of D-7-(2-naphthylglycylamido)-3-cephem-4-carboxylic acid.

IR (KBr): 1771.75 cm$^{-1}$ (β-lactam);

NMR (TFA$_d$1) δ3.55 (q, 2H); δ4.08 (s, 1H); δ5.6–6.0 (m, 2H); δ7.5–8.1 (m, 7H).

EXAMPLE 13

7-[α-Methoxyimino-α-(8-chloro-2-naphthyl)acetamido]-3-methyl-3-cephem-4-carboxylic acid Four hundred twenty milligrams of α-methoxyimino-α-(8-chloro-2-naphthyl)acetic acid were converted to the acid chloride by reaction with excess chlorine and 500 mg of triphenyl phosphite in 20 ml of dichloromethane. The reaction mixture was added in one portion to a stirred solution of 350 mg of 7-amino-3-methyl-3-cephem-4-carboxylic acid in 5 ml of dichloromethane containing 2 ml of bis(trimethylsilyl)trifluoroacetamide. The reaction mixture was stirred at 25° C. for six hours and then diluted by addition of 20 ml of methanol. The solvent was removed by evaporation under reduced pressure to provide 7-[α-methoxyimino-α-(8-chloro-2-naphthyl)acetamido]-3-methyl-3-cephem-4-carboxylic acid. The product thus formed is dissolved in formic acid containing zinc metal dust to give, following isolation and purification, 7-(8-chloro-2-naphthyl)-glycylamido-3-methyl-3-cephem-4-carboxylic acid.

The following compounds are similarly prepared:
7-(8-nitro-2-naphthyl)glycylamido-3-chloro-3-cephem-4-carboxylic acid;
7-(8-hydroxy-2-naphthyl)glycylamido-3-methoxymethyl-3-cephem-4-carboxyliczacid;
7- 8-amino-2-naphthyl)glycylamido-3-methyl-3-cephem-4-carboxylic acid; and
7-(8-methoxy-2-naphthyl)glycylamido-3-methyl-3-cephem-4-carboxylic acid.

The naphthylglycyl cephalosporins provided by this invention are valuable antibiotic substances, or intermediates therefor. The compounds, while active against a broad spectrum of gram-positive and gram-negative bacilli, are particularly effective against a wide variety of gram-positive bacilli. The antibiotic compounds are thus especially useful for treating infections in animals caused by gram-positive microorganisms. The compounds are particularly effective in the treatment of upper respiratory infections and similar diseases caused by *H. influenza, S. aureus, S. pyogenes,* and the like. The compounds are also effective in the treatment of diseases caused by anaerobic cocci such as *Peptostreptococcus anaerobius, Peptostrept. intermedius, Peptostrept. productus, Peptococcus saccharolyticus, P. prevotii, P. avaerobius, Propionibacterium acnes, Fusobacterium necrophorum,* and the like.

A typical and preferred compound provided by this invention is 7-(2-naphthylglycylamido)-3-methyl-3-cephem-4-carboxylic acid, the compound of Example 3. The antibacterial activity of this compound and several others of the invention has been determined in standard in vitro agar dilution assays against a variety of gram positive microorganisms. The following Tables present typical minimum inhibitory concentrations (MIC's) in µg/ml for the compounds when evaluated against the indicated microorganisms. MIC's for several known compounds are also presented for comparison.

TABLE I

| | | | | Agar Dilution MIC (µg/ml) | | | | | | | |
|---|---|---|---|---|---|---|---|---|---|---|---|
| | | Ampi- | Cepha- | Compound of | | | | | | | |
| Organism | Strain | cillin | lexin | Ex. 3 | Ex. 5A | Ex. 5B | Ex. 6 | Ex. 7 | Ex. 10 | Ex. 11 | Ex. 12 |
| Staph. aureus | X1.1 | 0.25 | 4 | 0.5 | 0.25 | 8 | 1 | 0.25 | 0.25 | 0.5 | 4 |
| | V41 | 32 | 128 | 8 | 16 | >128 | 32 | 8 | 16 | 8 | 64 |
| | X400 | 128 | 128 | 64 | 128 | >128 | 128 | 64 | 64 | 32 | 128 |
| | S13E | 64 | 128 | 8 | 16 | >128 | 32 | 8 | 16 | 8 | 64 |
| Staph. epi | EPI1 | 8 | 32 | 1 | 2 | 32 | 8 | 4 | 4 | 4 | 32 |
| | 222 | 0.25 | 8 | 0.5 | 0.25 | 4 | 2 | 0.5 | 1 | 1 | 4 |
| Strep. A | C203 | 0.03 | 0.5 | 0.5 | 0.125 | 4 | 0.125 | 0.06 | 0.125 | 0.125 | 0.5 |
| Strep. PN | PARK | 0.03 | 2 | 0.5 | 0.125 | >128 | >138 | 0.25 | 0.125 | 0.25 | 1 |
| H. influ. | BRUN | 0.5 | 8 | 8 | 4 | >128 | >128 | 32 | 16 | 8 | 64 |
| | 251 | 16 | 8 | 2 | 2 | 16 | 32 | 2 | 4 | 4 | 16 |
| Klebsiella | X26 | 16 | 4 | 2 | 2 | 2 | 8 | 8 | 4 | 4 | 16 |

TABLE II

| | | Expanded Spectrum MIC (µg/ml) | | | | |
|---|---|---|---|---|---|---|
| | | Compound of | | | | |
| Organism | Strain | Ex. 3 | Ex. 7 | Ex. 8 | Ex. 10 | Ex. 11 |
| Staph. epi | EPI1 | 8 | 8 | 4 | 4 | 4 |
| | 270 | 4 | 4 | 2 | 4 | 4 |
| | 219 | 0.5 | 0 | 0.5 | 5 | 0.5 |
| | 269 | 2 | 4 | 2 | 2 | 2 |
| | 285 | 2 | 2 | 1 | 2 | 2 |
| | 286 | 1 | 1 | 0.5 | 0.5 | 1 |
| Staph. aureus | S224 | 0.5 | 0.5 | 0.5 | 0.5 | 0.5 |
| | S225 | 0.5 | 0.5 | 0.5 | 0.5 | 0.5 |
| | S226 | 1 | 1 | 1 | 1 | 1 |
| | S227 | 1 | 0.5 | 0.5 | 1 | 0.5 |
| | S228 | 0.5 | 0.5 | 0.5 | 0.5 | 0.5 |
| | S229 | 1 | 1 | 1 | 1 | 1 |
| | S230 | 0.5 | 0.5 | 0.5 | 0.5 | 0.5 |
| | S231 | 0.5 | 0.25 | 0.5 | 0.25 | 0.5 |
| | S234 | 1 | 1 | 1 | 1 | 1 |
| | S237 | 1 | 0.5 | 0.5 | 1 | 1 |
| | S238 | 1 | 1 | 1 | 1 | 1 |
| | S239 | 1 | 1 | 1 | 1 | 1 |
| H. influ. | C.L. | 8 | 32 | 8 | 8 | 4 |
| | 76 | 2 | 16 | 8 | 4 | 2 |
| | HESS | 8 | 32 | 8 | 8 | 4 |
| | STEL | 8 | >64 | >64 | 16 | >64 |
| | 312 | 8 | 8 | 8 | 4 | 4 |
| | R465 | 8 | 32 | 16 | 16 | 16 |
| | 1930 | 8 | 16 | 16 | 8 | 4 |
| | 4842 | 4 | 8 | 8 | 4 | 4 |
| | 1683 | 2 | 2 | 4 | 2 | 2 |
| | M366 | 8 | >64 | >64 | 16 | >64 |
| | M370 | 4 | 8 | 4 | 4 | 4 |
| | M371 | 4 | 8 | 4 | 4 | 2 |
| | 105 | 4 | 8 | 8 | 4 | 4 |
| | 158 | 4 | 4 | 8 | 4 | 2 |
| | 164 | 4 | 4 | 8 | 4 | 2 |
| | 171 | 4 | 8 | 8 | 4 | 4 |

TABLE II-continued

| | | Expanded Spectrum MIC (µg/ml) | | | | |
|---|---|---|---|---|---|---|
| | | Compound of | | | | |
| Organism | Strain | Ex. 3 | Ex. 7 | Ex. 8 | Ex. 10 | Ex. 11 |
| | 169 | 4 | 8 | 8 | 4 | 4 |

TABLE III

| | | Expanded Spectrum MIC (µg/ml) | | |
|---|---|---|---|---|
| | | | | Compound of |
| Organism | Strain | Cephalexin | Cefaclor | Example 3 |
| S. Aureus | 8725 | 2 | 2 | 0.25 |
| | 8787 | 1 | 1 | 0.25 |
| | 9050 | 2 | 2 | 0.5 |
| | 9290 | 4 | 8 | 1.0 |
| | 9767 | 4 | 2 | 1.0 |
| | 8438 | 1 | 1 | 0.25 |
| | 9136 | 2 | 2 | 0.25 |
| B. Fragilis | 10817 | 16 | 64 | 2 |
| | 180-821 | 16 | 64 | 2 |
| | 10695 | 64 | 32 | 4 |
| | 107268 | 16 | 16 | 8 |
| | 107266 | 32 | 16 | 16 |
| | 10750 | 64 | >64 | 16 |
| | 10774 | >64 | >64 | 16 |
| | 10837 | 16 | >64 | 16 |
| | 10683 | >64 | 16 | 32 |
| | 10668 | >64 | 64 | 32 |
| H. Influenza | 101 | 8 | 2 | 4 |
| | 102 | 16 | 16 | 32 |
| | 103 | 16 | 2 | 4 |
| | 104 | 16 | 1 | 1 |
| | 105 | 4 | 1 | 2 |
| | 106 | 8 | 2 | 1 |
| | 107 | 8 | 2 | 4 |
| | 108 | 8 | 1 | 4 |
| | 109 | 16 | 2 | 4 |
| | 110 | 8 | 1 | 4 |
| | 111 | 16 | 1 | 1 |

TABLE IV

Susceptibility of *Anaerobic Cocci* Isolates by the Agar-Dilution Method-24 hour MIC's (µg/ml)

| Anaerobic Coccus | | Cefoxitin | Compound of Example 3 |
|---|---|---|---|
| Peptococcus Asaccharolyticus | 1344 | 0.25 | ≦0.125 |
| Peptococcus Constellatus | 1468 | 8 | 0.25 |
| P. magnus | 1401 | 2 | 0.25 |
| P. magnus | 1477 | 0.5 | 0.5 |
| P. prevoti | 1293 | 1.0 | 0.5 |
| Peptostreptococcus anaerobius | 8 | 0.25 | ≦0.125 |
| Peptostreptococcus anaerobius | 52 | 2 | 0.25 |

TABLE IV-continued

Susceptibility of *Anaerobic Cocci* Isolates by the Agar-Dilution Method-24 hour MIC's (µg/ml)

| Anaerobic Coccus | | Cefoxitin | Compound of Example 3 |
|---|---|---|---|
| *Peptostreptococcus anaerobius* | 1477 | 1 | ≦0.125 |
| *Peptostreptococcus intermedius* | 1264 | 1.0 | 1.0 |
| *Peptostreptococcus intermedius* | 1524 | 4.0 | 1.0 |
| *Peptostreptococcus intermedius* | 1624 | 4.0 | 1.0 |
| *Bacteroides fragilis* | 3625 | 16 | 16 |
| | 7371A | 8 | 16 |
| | 200 | 8 | 32 |
| | 206 | 16 | 16 |
| | 19671 | 16 | >64 |
| | 19681 | 32 | 16 |
| *Propionibacterum acnes* | 44 | 2 | 4 |
| | 79 | 8 | 8 |
| | 101 | 4 | 8 |
| | 104 | 4 | 8 |
| | 105 | 2 | 4 |
| | 5191 | ≦0.06 | 0.25 |
| | 5227 | 2 | 0.25 |
| | 5228 | 4 | 8 |
| | 5229 | 2 | 8 |
| | 5246 | 4 | 8 |

The data in the above Tables clearly demonstrate the potent antibacterial activity possessed by the compounds of this invention.

In addition to possessing potent antibacterial activity against a wide variety of microorganisms, particularly gram positive organisms and anaerobes, the compounds of this invention also have demonstrated very favorable pharmacokinetics in animals. For example, when 7-(2-naphthylglycylamido)-3-methyl-3-cephem-4-carboxylic acid was administered to rats at an intravenous dose of 20 mg/kg, the plasma concentration after one hour was 18.6 µg/ml; after four hours, 14.1 µg/ml; and after twenty-four hours, the plasm level was still measured as 1.96 µg/ml. The compound is efficiently orally absorbed in rodents and exhibits higher and longer blood levels than cefaclor and cephalexin.

The compounds of the invention also have good stability to β-lactamases. Table IV shows the results of comparative studies of several cephalosporins (lower numbers mean greater stability to the indicated β-lactamase).

TABLE V

Stability to β-lactamases

| | Organism | | | | |
|---|---|---|---|---|---|
| | 265A | PS185 | TEM | 1082E | 1313G |
| cefaclor | 138 | 71 | 23 | 65 | 4605 |
| cephalexin | 72 | 37 | 1 | 6 | 254 |
| 7-(2-naphthyl-glycylamido)3-methyl-3-cephem-4-carboxylic acid | 50 | 25 | 3 | 26 | 256 |

The favorable pharmacokinetics of the compounds provided by this invention, coupled with their excellent oral antibacterial activity and stability toward β-lactamases, make them particularly attractive agents for the treatment of a number of diseases of bacterial origin. The compounds are especially well suited for the treatment of out-patients, and especially for subjects suffering from mild upper respiratory infections caused by gram positive microorganisms.

The treatment of animals suffering from bacterial diseases, or suspected of developing a bacterial infection, is thus another embodiment of this invention. The antibacterial method of treatment provided by this invention will be practiced by administering an antibacterially effective amount of a naphthylglycyl cephalosporin antibiotic as defined herein to an animal in need of treatment. The method can be practiced therapeutically or prophalactically. The amount of active antibiotic to be administered according to the method will vary depending upon the particular compound selected for use, the severity of the disease being treated or guarded against, the individual undergoing treatment, and related factors commonly encountered with such treatments. Normally, however, the compounds will be administered at a dose of about 0.5 to about 50 mg/kg of animal body weight, and more preferably at a rate of about 1 to about 10 mg/kg. Such amounts will be administered once or twice each day, or more often as needed to treat the particular disease or subject undergoing treatment according to the present method. A typical daily dose for an average adult human will be about 200 to about 500 mg per day.

The antibiotic compounds provided by this invention are active by both the oral and parenteral routes of administration, and accordingly can be formulated for any such desired route of administration. Such formulations constitute yet another embodiment of this invention. The formulations of this invention will comprise from about 0.1 to about 95 percent by weight of an active naphthylglycyl cephalosporin anti-biotic of the invention, admixed with a pharmaceutically acceptable carrier, diluent or excipient therefor. Typical formulations will contain from about 10 to about 60 percent by weight of active ingredient, and more preferably about 20 to about 50 percent.

For convenient oral administration, the compounds can be admixed with any of a number of diluents, excipients and carriers commonly employed in oral formulations, and molded into tablets, pills, troches, or encapsulated into gelatin capsules. Typical carriers, diluents and excipients commonly employed include potato starch, corn starch, sucrose, dextrose, microcrystalline cellulose, dicalcium phosphate, alginic acid, acacia; lubricants such as magnesium stearate; binders such as gum tragacanth or gelatin; and flavoring agents such as peppermint oil, cherry or strawberry flavoring, oil of wintergreen, and the like. The compounds can also be formulated as syrups or elixirs employing common diluents such as a fatty oil, methyl or propylparabens, suitable dyes and flavoring agents. The compounds can also be formulated in the form of a buccal seal, logenze or other suitable device for sustained controlled delivery of the active ingredient over a prolonged period.

The antibiotics of the invention can also be formulated for parenteral administration, for example via the intravenous, intramuscular or subcutaneous routes, as well as the transdermal route. Such compositions normally will contain from about 0.1 to about 20.0 percent by weight of active ingredient. Typical excipients, diluents and carriers for parenteral formulations include isotonic saline, dilute aqueous dextrose, the polyhydric aliphatic alcohols or mixtures thereof, for instance glycerin, propylene glycol, polyethylene glycol, and the like. Parenteral solutions may also contain preservatives such as phenethylalcohol, methyl and propyl parabens, thimerosal and the like. If needed, about 0.05 to about 0.20 percent by weight of an antioxidant such as sodium metabisulfite or sodium bisulfite can also be eemployed. For intravenous use, preferred formulations will employ an initial concentration down to about 0.05 to about 0.25 mg/ml of active ingredient, and for intramuscular injection, a preferred concentration of active ingredient is about 0.25 to about 0.50 mg/ml.

The following examples illustrate typical formulations provided by the invention.

EXAMPLE 14

| Formulation of Oral Suspension | |
|---|---|
| Ingredient | Amount |
| Sodium D-7-(2-Naphthylglycylamido)-3-chloro-3-cephem-4-carboxylate | 500 mg |
| Sorbitol solution (70% N.F.) | 40 ml |
| Sodium benzoate | 150 mg |
| Saccharin | 10 mg |
| Cherry flavor | 50 mg |
| Distilled water qs ad | 100 ml |

The sorbitol solution is added to 40 ml of distilled water and the naphthylglycyl cephalosporin is suspended thereon. The saccharin, sodium benzoate, and flavoring are added and dissolved. The volume is adjusted to 100 ml with distilled water. Each ml of syrup contains 5 mg of the antibiotic naphthylglycyl cephalosporin. This oral formulation is ideally suited for pediatric use.

EXAMPLE 15

| Preparation of 250 mg capsule | |
|---|---|
| Ingredient | Amount |
| 7-(6-Chloronaphth-2-ylglcylamido)-3-methyl-3-cephem-4-carboxylic acid | 250 mg |
| Lactose | 150 mg |
| Corn starch | 100 mg |
| | 500 mg |

The ingredients are blended to uniformity and encapsulated into gelatin capsules. Such capsules are orally administered at the rate of about one each day for the treatment of upper respiratory bacterial infections, including pharyngitis and tonsillitis.

EXAMPLE 16

Preparation of Parenteral Solution

In a solution of 700 ml of propylene glycol and 200 ml of distilled water for injection is dissolved 20.0 grams of D-7-(2-naphthylglycylamido)-3-methyl-3-cephem-4-carboxylic acid, hydrochloride. The pH of the solution is adjusted to 5.5 with hydrochloric acid, and the volume is made up to 1000 ml with distilled water. The formulation is sterilized, filled into 5.0 ml ampoules each containing 2.0 ml (representing 40 mg of active ingredient) and sealed under nitrogen.

We claim:
1. A compound of the formula

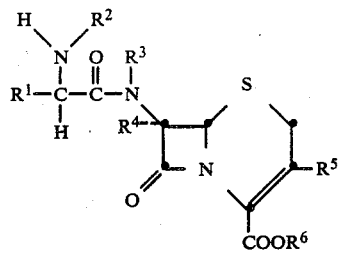

wherein:
$R^1$ is

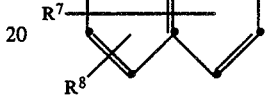

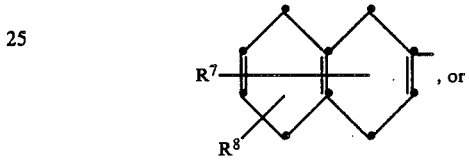

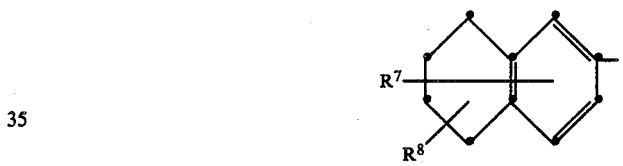

in which $R^7$ and $R^8$ independently are hydrogen, halo, hydroxy, $C_1$–$C_4$ alkyl, $C_1$–$C_4$ alkyoxy, nitro, amino, $C_1$–$C_4$ alkanoylamino, $C_1$–$C_4$ alkylsulfonylamino, or when $R^7$ and $R^8$ are on adjacent carbon atoms, they can be taken together to form methylenedioxy;

$R^2$ is hydrogen, an amino protecting group, and $R^3$ is hydrogen, or $R^2$ and $R^3$ taken together are

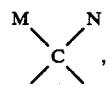

where M and N independently are $C_1$–$C_4$ alkyl;
$R^4$ is hydrogen, methoxy or methylthio;
$R^5$ *is hydrogen, methoxy, methyl, halo, or methoxymethyl;*
$R^6$ is hydrogen, a salt forming cation group, or a carboxy protecting group; and the pharmaceutically acceptable acid addition salts thereof.

2. The compound of claim 1 wherein $R^2$ and $R^3$ are taken together to form

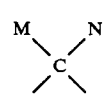

3. The compound of claim 1 wherein $R^1$ is

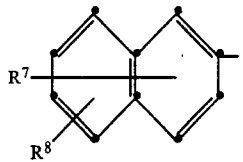

4. The compound of claim 3 wherein $R^7$ is hydrogen or halo.

5. The compound of claim 4 wherein $R^7$ is hydrogen.

6. the compound of claim 5 wherein $R^4$ is hydrogen.

7. The compound of claim 6 wherein $R^5$ is methyl or chloro.

8. the compound of claim 7 wherein $R^6$ is hydrogen or a salt forming cation.

9. The compound of claim 8, said compound being D-7-(2-naphthyl)glycylamido-3-methyl-3-cephem-4-carboxylic acid.

10. The compound of claim 8 wherein $R^8$ is halo.

11. The compound of claim 10 wherein $R^8$ is chloro.

12. The compound of claim 10 wherein $R^8$ is fluoro.

13. The compound of claim 8 wherein $R^8$ is hydroxy.

14. The compound of claim 8 wherein $R^8$ is $C_1$–$C_4$ alkoxy.

15. The compound of claim 8 wherein $R^8$ is amino.

16. The compound of claim 6 wherein $R^5$ is hydrogen.

17. The compound of claim 6 wherein $R^5$ is methoxymethyl.

18. The compound of claim 6 wherein $R^5$ is methoxy.

19. The compound of claim 1 wherein $R^1$ is

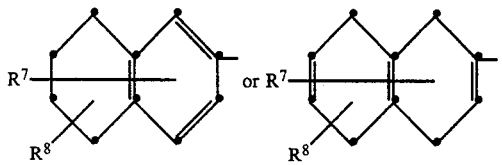

20. The compound of claim 19 wherein $R^7$ is hydrogen.

21. The compound of claim 20 wherein $R^4$ is hydrogen.

22. The compound of claim 21 wherein $R^5$ is methyl or chloro.

23. The compound of claim 22 wherein $R^6$ is hydrogen or a salt forming cation.

24. A method of treating bacterial infections in animals comprising administering an effective amount of an antibacterial compound of claim 1.

25. The method of claim 24 employing a compound wherein $R^2$, $R^3$ and $R^4$ all are hydrogen.

26. The method of claim 25 employing a compound wherein $R^6$ is hydrogen or a salt forming cation.

27. The method of claim 26 employing a compound wherein $R^5$ is methyl or chloro.

28. The method of claim 27 employing a compound wherein $R^1$ is

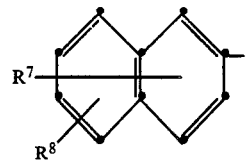

29. The method of claim 28 employing a compound wherein $R^7$ is hydrogen.

30. The method of claim 29 employing D-7-(2-naphthyl)-glycylamido-3-methyl-3-cephem-4-carboxylic acid.

31. The method of claim 29 employing a compound wherein $R^8$ is methoxy.

32. The method of claim 29 employing a compound wherein $R^8$ is chloro.

33. A pharmaceutical formulation comprising an antibacterially effective amount of a compound of claim 1 admixed with a pharmaceutical carrier, diluent or excipient.

34. The formulation of claim 33 employing a compound wherein $R^2$, $R^3$ and $R^4$ all are hydrogen.

35. The formulation of claim 34 employing a compound wherein $R^6$ is hydrogen or a salt forming cation.

36. The formulation of claim 35 employing a compound wherein $R^5$ is methyl or chloro.

37. The formulation of claim 36 employing a compound wherein $R^1$ is

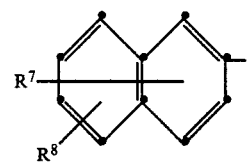

38. The formulation of claim 37 employing a compound wherein $R^7$ is hydrogen.

39. The formulation of claim 38 employing a compound wherein $R^8$ is hydrogen.

40. The formulation of claim 38 employing a compound wherein $R^8$ is halo.

* * * * *